US008765907B2

(12) United States Patent
Imhoff et al.

(10) Patent No.: US 8,765,907 B2
(45) Date of Patent: Jul. 1, 2014

(54) PRODUCTION AND USE OF ANTITUMORAL ANTIBIOTIC AND INSECTICIDAL CYCLODEPSIPEPTIDES

(75) Inventors: Johannes Imhoff, Preetz (DE); Inga Knopf-Kajahn, Gettorf (DE); Gerhard Lang, Courgevaux (CH); Jutta Wiese, Eutin (DE); Arne Peters, Hondörf (DE)

(73) Assignee: Geomar Helmholtz-Zentrum fur Ozeanforschung Kiel, Kiel (DE)

( * ) Notice: Subject to any disclaimer, the term of this patent is extended or adjusted under 35 U.S.C. 154(b) by 265 days.

(21) Appl. No.: 13/376,587

(22) PCT Filed: Apr. 30, 2010

(86) PCT No.: PCT/DE2010/000498
§ 371 (c)(1),
(2), (4) Date: Feb. 17, 2012

(87) PCT Pub. No.: WO2010/142258
PCT Pub. Date: Dec. 16, 2010

(65) Prior Publication Data
US 2013/0210711 A1    Aug. 15, 2013

(30) Foreign Application Priority Data
Jun. 11, 2009 (DE) .......................... 10 2009 025 119

(51) Int. Cl.
*C07K 7/02* (2006.01)
*A61K 38/08* (2006.01)
*C07K 11/02* (2006.01)
*A01N 43/72* (2006.01)
*C12P 21/02* (2006.01)
*C07K 7/06* (2006.01)
*A61K 38/00* (2006.01)

(52) U.S. Cl.
CPC ............... *C07K 11/02* (2013.01); *A01N 43/72* (2013.01); *C12P 21/02* (2013.01); *A61K 38/00* (2013.01); *C07K 7/06* (2013.01)
USPC .............. 530/317; 530/323; 514/2.4; 514/2.9

(58) Field of Classification Search
None
See application file for complete search history.

(56) References Cited

U.S. PATENT DOCUMENTS

| | | | |
|---|---|---|---|
| 5,569,668 | A | 10/1996 | Webster et al. |
| 5,827,872 | A | 10/1998 | Webster et al. |
| 6,048,838 | A | 4/2000 | Ensign et al. |
| 6,174,860 | B1 | 1/2001 | Kramer et al. |
| 6,277,823 | B1 | 8/2001 | Kramer et al. |
| 6,316,476 | B1 | 11/2001 | Webster et al. |
| 6,583,171 | B1 | 6/2003 | Webster et al. |
| 6,841,165 | B1 | 1/2005 | Jarrett et al. |
| 7,214,525 | B1 | 5/2007 | Jarrett et al. |
| 7,285,632 | B2 | 10/2007 | Apel-Birkhold et al. |
| 2008/0104731 | A1 | 5/2008 | Sheets et al. |

FOREIGN PATENT DOCUMENTS

| | | |
|---|---|---|
| DE | 102 52 284 | 6/2004 |
| EP | 0 192 713 B1 | 11/1991 |
| EP | 1 130 970 B1 | 2/2003 |
| EP | 1 351 977 B1 | 8/2004 |
| EP | 1351977 B1 * | 8/2004 |
| EP | 1 143 800 B1 | 8/2006 |
| WO | WO 2005/034982 A1 | 4/2005 |

OTHER PUBLICATIONS

Dict.cc. German-English Dictionary—Adiposita/Fittlebigkeit/obesity, May 12, 2010.*
Akhurst et al., "Morphological and functional dimorphism in *Xenorhabdus spp.*, bacteria symbiotically associated with the insect pathogenic *Neoaplectana* and *Heterorhabditis*," J. Gen. Microbiol., 1980, vol. 121, pp. 303-309.
Baki et al., "A high throughput luminescent assay for glycogen synthase kinase-3beta inhibitors," Assay and Drug Development Technologies, 2007, vol. 5, pp. 75-83.
Birman et al., "Determination of acetylcholinesterase activity by a new chemiluminescence assay with natural substrate," Biochemical Journal, 1985, vol. 225, pp. 825-828.
Dengler et al., "Development of a propidium iodide fluorescence assay for proliferation and cytoxicity assay," Anti-Cancer Drugs, 1995, vol. 6, pp. 522-532.
Hohmann et al., "Caboxamycin, a new antibiotic of the benzoxazole family produced by the deep-sea strain *Streptomyces sp.* NTK 937," 2009, The Journal of Antibiotics, vol. 62, pp. 99-104.
Johnigk et al., "Liquid culture mass production of biocontrol nematodes, *Heterorhabditis bacteriophora* (Nematoda: Rhabditida): improved timing of dauer juvenile inoculation," Appl. Microbiol. Biotechnol., 2004, vol. 64, pp. 651-658.
Lang et al., "Linear and cyclic peptides from the entomopathogenic bacterium *Xenorhabdus nematophilous*," J. Nat. Prod., 2008, vol. 71, pp. 1074-1077.
Lang et al., "New pentaenes from the sponge-derived marine fungus *Penicillium rugulosum*: structure determination and biosynthetic studies," Tetrahedron, 2007, vol. 63, pp. 11844-11849.
Siegmund et al., "Death receptor-induced signaling pathways are differentially regulated by gamma interferon upstream of caspase 8 processing," Mol. Cell. Biol., 2005, vol. 25, pp. 6363-6379.
Thaler et al., "Purification and characterization of xenorhabdicin, a phage tail-like bacteriocin from the lysogenic strain F1 of *Xenorhabdus nematophilus*," Appl. Environ. Microbiol., 1995, vol. 61, pp. 2049-2052.
International Search Report for PCT/DE2010/000498.

* cited by examiner

*Primary Examiner* — James H Alstrum Acevedo
*Assistant Examiner* — Jeanette Lieb
(74) *Attorney, Agent, or Firm* — Kilpatrick Townsend & Stockton LLP

(57) ABSTRACT

The invention relates to a compound of the general structure (I), where R is a hydrogen atom (II) or an unsubstituted, monosubstituted or polysubstituted $C_1$-$C_{20}$-alkyl, wherein the alkyl is straight, branched, cyclic and/or partially unsaturated, or an unsubstituted, monosubstituted or polysubstituted phenyl group.

19 Claims, No Drawings

PRODUCTION AND USE OF ANTITUMORAL ANTIBIOTIC AND INSECTICIDAL CYCLODEPSIPEPTIDES

The present application is a 371 national phase application of PCT/DE2010/000498, filed Apr. 30, 2010, which application claims priority to DE 10 2009 025 119.7, filed Jun. 11, 2009, the disclosures of which are hereby incorporated by reference in their entireties for all purposes.

The present invention relates to cyclic peptides, the Xenobovides, which are suitable for the production of medicaments for the treatment of infectious, tumour-based, neurological and inflammation-based diseases as well as diabetes. An additional area of application of the invention is the production of insecticides and pesticides. The invention further relates to a method for the production of these compounds by fermentation of a bacterium and chromatographic purification of the bacterial extract, as well as to their use as a medicament, insecticide and pesticide.

Certain genera of nematodes comprise insecticidal bacterial symbionts. The nematodes living in soil trace insects in nature and pierce the surface of the insects, so that pathogenic bacteria are injected into the hemocoel of the insect. These bacteria produce antibiotics, enzymes and toxins that kill the insect. The nematodes present in the insect reproduce, acquire further bacteria and are liberated from the decomposing carcass to locate new insects.

The bacteria of the genus *Xenorhabdus*, which are symbiotically associated with *Steinernema* nematodes, are known as a source of a large quantity of biologically active substances. From these entomonopathogenic bacteria, different proteins have been isolated that are toxic for insects. This is, e.g., the case for TC-proteins ("toxin complex proteins") as described in U.S. Pat. No. 7,285,632 B2 or in US 2008/0104731 A1, for "TC-like" proteins (EP 1 130 970 B1, EP 1 143 800 B1) or for a number of other toxin proteins (U.S. Pat. No. 6,048,838, U.S. Pat. No. 6,174,860 B1, U.S. Pat. No. 6,277,823 B1, U.S. Pat. No. 7,214,525 B1, U.S. Pat. No. 6,841,165 B1). Several anti-bacterially active substances isolated from these bacteria are also known: pseudopeptide (EP 1 351 977 B1), the peptide xenorhabdicin (Thaler et al., 1995, Purification and characterization of xenorhabdicin, a phage tail-like bacteriocin from the lysogenic strain F1 of *Xenorhabdus nematophilus*. Appl. Environ. Microbiol. 61:2049-2052), the xenorhabdines (EP 0 192 713 B1), the xenocoumacines (EP 0 192 713 B1), the nematophines (U.S. Pat. No. 5,569,668), the xenomines (U.S. Pat. No. 5,827,872) or the xenorxides (U.S. Pat. No. 6,316,476 B1). Xenomines and xenorxides additionally have anti-neoplastic activity (U.S. Pat. No. 6,583,171 B1).

Worldwide, there is an increasing need for new agents for the treatment of infectious, cancer and inflammatory diseases as well as diabetes and neurological diseases. Furthermore, there exists a need for new substances that can be applied as insecticides or pesticides.

Therefore, the present invention is based on the problem of providing further peptides that are effective antibiotically, antitumorally, anti-inflammatory, in lowering the blood sugar level, in increasing the acetylcholine level or effective insecticidally, or that inhibit the activity of the acetylcholine esterase, phosphodiesterase, protein tyrosine phosphatase or of the glycogen synthase kinase, or that are effective against pathogens of plant diseases, as well as showing a way for their production.

According to the invention, this problem is solved by the compound having the features of claim 1. The sub-claims represent advantageous embodiments of the invention.

Within a scientific program for the isolation of biologically active natural products from microorganisms, the inventors isolated and analyzed the bacterium *Xenorhabdus bovienii* from the nematode *Steinernema bibionis*.

The peptides Xenobovide A, B and C, which are preferred according to the invention, were isolated from cultures of the bacterium *Xenorhabdus bovienii* by fast centrifugal partitioning chromatography (FCPC) and preparative HPLC.

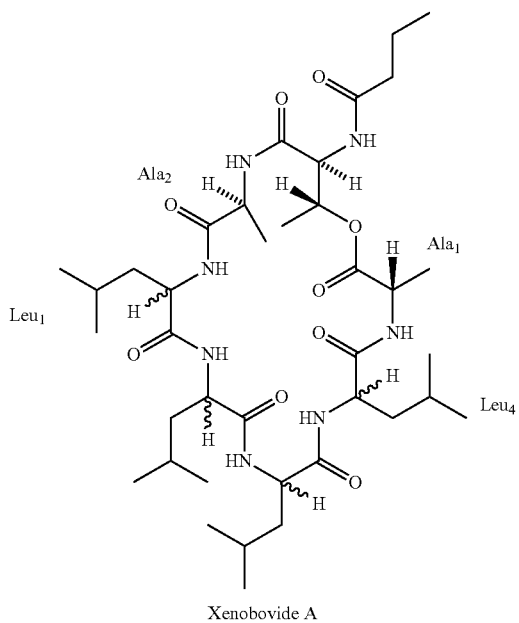

Xenobovide A

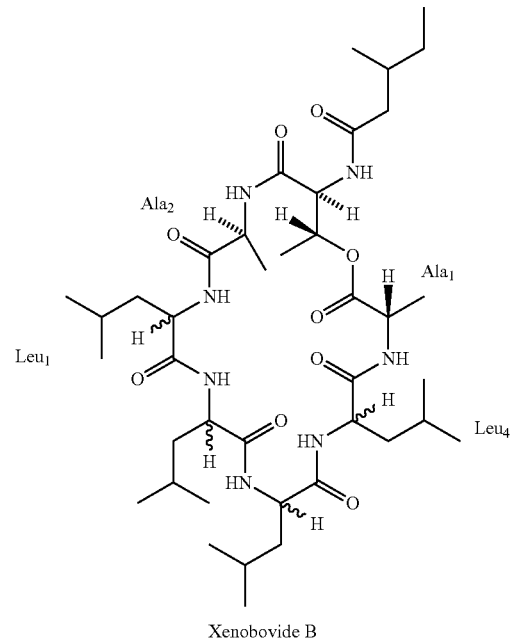

Xenobovide B

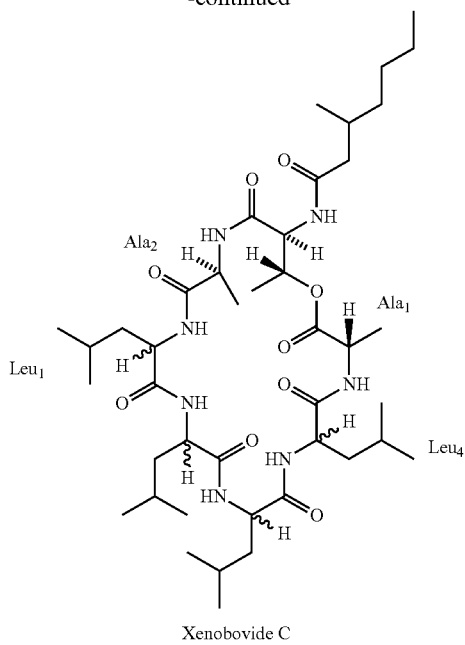

Xenobovide C

The physical data of Xenobovide A, B and C is depicted in the attached tables 1, 2 and 3, wherein table 1 shows the NMR data (600 MHz, DMSO) of Xenobovide A, table 2 shows the NMR data (600 MHz, DMSO) of Xenobovide B and table 3 shows the NMR data (600 MHz, DMSO) of Xenobovide C.

The substances according to the invention in the specific embodiments, Xenobovide A, B and C, have the capability of inhibiting the growth of the gram-positive bacterium *Staphylococcus xyloses*. Xenobovide B and C additionally show a significant inhibitory effect against the gram-positive bacterium *Bacillus subtilis* (Example 3).

The growth of the phytopathogenic bacterium *Xanthomonas campestris*, which is inter alia the pathogen of the black rot of crucifers in *Brassica*, is inhibited by Xenobovide A (Example 4).

The substances according to the invention, Xenobovide A, B and C, further show different, significant inhibitory effects against tumour cell lines, especially against cell lines of human gastric tumour, lung tumour, breast cancer, melanoma, pancreas tumour, kidney tumour and intestinal tumour (see Example 5).

Xenobovide A inhibits the activity of the following enzymes:

Acetylcholine esterase (Example 6): inhibitors of the degradation of acetylcholine may be used in the treatment or prevention of neurological diseases such as Myasthenia Gravis or Morbus Alzheimer.

Phosphodiesterase PDE-4B2 (Example 7): PDE4-inhibitors are proven anti-inflammatory agents, especially in inflammatory lung diseases, such as asthma, chronic obstructive bronchitis and lung emphysema as well as in rhinitis. These inhibitors may additionally have an anti-depressive effect, and were suggested for use as psychotropic drugs. Furthermore, PDE-4 inhibitors are able to attenuate the virulence of HIV and could therefore be used in AIDS therapy.

Protein tyrosine phosphatase IB (Example 8): protein tyrosine phosphatase 1B is an effective target for the treatment of diabetes and obesity.

Xenobovide A as well as Xenobovide B additionally inhibit the activity of the glycogen synthase kinase 3beta (Example 9). The inhibition of this enzyme may be involved in the treatment of Morbus Alzheimer and other acute or chronic neurodegenerative diseases, as well as diabetes and adipositas, bipolar disorders, schizophrenia, alopecia and cancer diseases.

The insecticidal effect of Xenobovide A, B and C was shown in larvae of the wax moth, a parasite in beekeeping (Example 10).

The propagation of *Xenorhabdus bovienii* as well as the purification of Xenobovide A, B and C from cultures of the bacterium, and the determination of the biological activity are described in the following examples.

1) Biotechnological Production of Xenobovides from *Xenorhabdus bovienii*

*X. bovienii* was isolated from the nematode *Steinernema bibionis* according to Akhurst et al. (1980, Morphological and functional dimorphism in *Xenorhabdus* spp., bacteria symbiotically associated with the insect pathogenic nematodes, *Neoaplectana* and *Heterorhabditis*. J. Gen. Microbiol. 121: 303-309). Cultivation was carried out for 36 hours in a 20 L-fermenter batch at 20° C. (Johnigk et al., 2004, Liquid culture mass production of biocontrol nematodes, *Heterorhabditis bacteriophora* (Nematoda: Rhabditida): improved timing of dauer juvenile inoculation. Appl. Microbiol. Biotechnol. 64:651-658).

2) Isolation of Xenobovides from the Bacterial Culture

The culture solution was harvested and shaken for a further 20 hours with XAD-16N adsorbant resin (Amberlite; 10 g/L culture solution). Then, the resin was washed with water (5 mL/g XAD) and subsequently eluted with methanol (2 mL/g XAD). The methanolic XAD extract was dried, resuspended in water (300 ml) and extracted three times with ethyl acetate (300 ml each). The pooled acetyl acetate phases were dried and separated by fast centrifugal partitioning chromatography (FCPC; Kromaton). For this, a two-phase solvent system ($H_2O$/MeOH/EtOAc/n-Heptan in the mixing ratio 49:51:49:51) was used, wherein the upper phase served as the stationary phase of the chromatography. The rotation speed of the FCPC was 1380 $min^{-1}$ and the flow rate was 6 mL/min. The cyclodepsipeptide containing fractions that eluted from 24 to 63 minutes were pooled, dried and further purified by preparative HPLC:

Separation column: Phenomenex Luna C18, 21.2×250 mm, 5 µm

Solvent: water+0.1% formic acid (A), acetronitrile+0.1% formic acid (B)

Gradient: 0 min-50% B, 8 min-100% B

Flow rate: 20 mL/min

Xenobovide A KW044 (15 mg), Xenobovide B KW12 (27 mg) und KW13 Xenobovide C (68 mg) eluted after 6.1, 8.0 und 8.5 min.

3) Antibacterial Effect of Xenobovide A, B or C

Xenobovide A, B and C, in a concentration of 65.3 µMol, 63.01 µMol and 61.9 µMol, respectively, inhibited the growth of the gram-positive bacterium *Staphylococcus xylosus* DSM 20267 by 83%, 81% and 32%, respectively. The testing of the antimicrobial activity was performed according to Lang et al. (2007, New pentaenes from the sponge-derived marine fungus *Penicillium rugulosum*: structure determination and biosynthetic studies. Tetrahedron 63:11844-11849).

Xenobovide B (63 µMol) and C (61.9 µMol) inhibited the growth of the gram-positive bacterium *Bacillus subtilis* (DSM 347) by 29% and 32%, respectively. The testing of the antimicrobial activity against *Bacillus subtilis* was performed according to Lang et al. (2007, New pentaenes from the sponge-derived marine fungus *Penicillium rugulosum*: structure determination and biosynthetic studies. Tetrahedron 63:11844-11849).

4) Antibacterial Activity of Xenobovide A Against Pathogens of Plant Diseases.

The phytopathogenic bacterium *Xanthomonas campestris* (DSM 2405), which is inter alia the pathogen of the black rot of crucifers in *Brassica*, was inhibited by Xenobovide A by 89%. The testing of the antimicrobial activity against *Xanthomonas campestris* was performed according to Lang et al. (2007, New pentaenes from the sponge-derived marine fungus *Penicillium rugulosum*: structure determination and biosynthetic studies. Tetrahedron 63:11844-11849).

5) Anti-Proliferative Effect of Xenobovide A, B, and C

Xenobovide A, B and C inhibited the proliferation of all six tested human tumour cell lines: GXF251L (gastric tumour cell line), LXF529L (lung tumour cell line), MAXF401NL (breast cancer cell line), MEXF462NL (melanoma cell line), PAXF1657L (pancreas tumour cell line) and RXF486L (kidney tumour cell line).

| Tumour cell line | Xenobovide A $IC_{50}$-value [μMol] | Xenobovide B $IC_{50}$-value [μMol] | Xenobovide C $IC_{50}$-value [μMol] |
|---|---|---|---|
| GXF251L | 1.6 | 2.5 | 3.0 |
| LXF529L | 8.5 | 9.7 | 7.8 |
| MAXF401NL | 2.1 | 3.2 | 8.5 |
| MEXF462NL | 2.7 | 5.3 | 9.4 |
| PAXF1657L | 3.5 | 2.9 | 10.3 |
| RXF486L | 12.0 | 14.5 | 7.6 |

The anti-proliferative effect was determined according to Dengler et al. (1995, Development of a propidium iodide fluorescence assay for proliferation and cytoxicity assay. Anti-Cancer Drugs 6:522-532).

The proliferation of the intestinal tumour cell line HT29 was inhibited by 7% by Xenobovide A (65.3 μMol) and by 78% by Xenobovide B (63 μMol), respectively. Xenobovide C was tested in a concentration of 12.3 μMol and showed an inhibition of the vitality of the cell line HT29 by 11%. These activities were determined after 48 hours incubation with the crystal violet assay (Siegmund, D. at al., 2005, Death receptor-induced signalling pathways are differentially regulated by gamma interferon upstream of caspase 8 processing. Mol. Cell. Biol. 25:6363-6379).

6) Inhibition of Acetylcholine Esterase by Xenobovide A

Xenobovide A inhibits the acetylcholine esterase with an $IC_{50}$-value of 53.6 μMol. Testing was performed according to Birman (1985, Determination of acetylcholinesterase activity by a new chemiluminescence assay with natural substrate. Biochemical Journal. 225:825-828).

7) Inhibition of the Phosphosdiesterase (PDE-4B2) by Xenobovide A

Xenobovide A in a concentration of 163 μg/mL inhibits the phosphodiesterase (PDE-4B2) by 46%. This enzyme test was carried out according to Hohmann et al. (2009, Caboxamycin, a new antibiotic of the benzoxazole family produced by the deep-sea strain *Streptomyces* sp. NTK 937. The Journal of Antibiotics. 62:99-104).

8) Inhibition of the Protein Tyrosine Phosphatase 1B (PTP1B) by Xenobovide A

Xenobovide A in a concentration of 26.1 μMol inhibits the protein tyrosine phosphotase 1B (PTB1B) by 59%. This enzyme test was carried out according to Hohmann et al. (2009, Caboxamycin, a new antibiotic of the benzoxazole family produced by the deep-sea strain *Streptomyces* sp. NTK 937. The Journal of Antibiotics. 62:99-104).

9) Inhibition of the Glycogen Synthase Kinase 3beta by Xenobovide A or B

Xenobovide A and B, in a concentration of 16.3 μMol and 15.6 μMol, respectively, inhibited the glycogen synthase kinase 3beta by 21% and 43%, respectively. The performance was according to Baki et al. (2007, A high throughput luminescent assay for glycogen synthase kinase-3beta inhibitors. Assay and Drug Development Technologies. 5:75-83) using the kinase-Glo Luminescent Kinase Assay Kit of the company Promega.

10) Insecticidal Effect Xenobovide A, B or C

The insecticidal effect was tested against the larvae of the wax moth, a pathogen in beekeeping. In four repeated experiments, the addition of Xenobovide A, B or C to the feed led to the death of all larvae used in the test. To test the oral toxicity, 1 mg substance/mL was dissolved in a 50% aqueous ethanol solution. Five larvae each were transferred into a plastic box (2 cm in diameter) and fed with 1 g food mixture (0.8 mL substance solution, 0.2 mL glycerine (86%) and 1 g wheat bran). The control group was fed with 1 g food mixture without addition of substance (0.4 mL aq. dest., 0.4 mL ethanol, 0.2 mL glycerine (86%) and 1 g wheat bran). The incubation of the larvae was at 35° C. for six days. Subsequently, the dead larvae were counted.

TABLE 1

NMR data (600 MHz, DMSO) of Xenobovide A
Colourless amorphous solid matter.
Optical activity: $[\alpha]^{25}_D$ −1.6° (c 0.25, MeOH)
HRESIMS: m/z 766.5075 $[M + H]^+$
(calculated for $C_{38}H_{68}N_7O_9$ 766.50785)

| Position | | $\delta_c$, mult. | $\delta_H$ (J in Hz) | COSY | HMBC |
|---|---|---|---|---|---|
| Thr | 1 | 169.1, qC | — | — | — |
| | 2 | 55.0, CH | 4.57, dd (2.1, 9.3) | 3, NH | 1, 3, 4, BA-1 |
| | 3 | 70.6, CH | 5.22, qd (2.1, 6.3) | 2, 4 | 1, 4, Ala$_1$-1 |
| | 4 | 17.3, CH$_3$ | 1.16, d (6.3) | 3 | 2, 3 |
| | NH | — | 7.69, d (9.4) | 2 | 2 |
| Ala$_1$ | 1 | 171.8, qC | — | — | — |
| | 2 | 48.5, CH | 4.15, m | 3, NH | 1, 3 |
| | 3 | 16.0, CH$_3$ | 1.29, d (6.9) | 2 | 1, 2 |
| | NH | — | 8.16, d (5.3) | 2 | 2, Leu$_4$-1 |
| Ala$_2$ | 1 | 172.2, qC | — | — | — |
| | 2 | 49.3, CH | 4.19, m (6.8) | 3, NH | 1, 3, Thr-1 |
| | 3 | 18.1, CH$_3$ | 1.26, d (7.2) | 2 | 1, 2 |
| | NH | — | 8.00, d (6.4) | 2 | 2, Thr-1 |
| Leu$_1$ | 1 | 173.5, qC | — | — | — |
| | 2 | 52.2, CH | 4.14, m | 3, NH | 1, 3, 4 |
| | 3 | 39.0, CH$_2$ | 1.58, m | 4 | 2, 4 |
| | 4 | 24.3$^b$, CH | 1.62$^b$, m | 3, 5, 6 | 3, 5, 6 |
| | 5 | 23.1$^b$, CH$_3$ | 0.88$^b$, m | 4 | 3, 4, 6 |
| | 6 | 23.1$^b$, CH$_3$ | 0.88$^b$, m | 4 | 3, 4, 5 |
| | NH | — | 7.58, d (6.1) | 2 | Ala$_2$-1 |
| Leu$_2$ | 1 | 172.0, qC | — | — | — |
| | 2 | 52.4, CH | 4.09, m | 3, NH | 1, 3, 4 |
| | 3 | 39.5, CH$_2$ | 1.62, m | 4 | 2, 4 |
| | 4 | 24.3$^b$, CH | 1.62$^b$, m | 3, 5, 6 | 3, 5, 6 |
| | 5 | 22.5$^b$, CH$_3$ | 0.92$^b$, m | 4 | 3, 4, 6 |
| | 6 | 22.5$^b$, CH$_3$ | 0.92$^b$, m | 4 | 3, 4, 5 |
| | NH | — | 7.53, d (6.8) | 2 | Leu$_1$-1 |
| Leu$_3$ | 1 | 171.6, qC | — | — | — |
| | 2 | 51.5, CH | 4.14, m | 3, NH | 1, 3, 4 |
| | 3 | 39.5, CH$_2$ | 1.58, m | 4 | 2, 4 |
| | 4 | 24.2$^b$, CH | 1.62$^b$, m | 3, 5, 6 | 3, 5, 6 |
| | 5 | 21.7$^b$, CH$_3$ | 0.85$^b$, m | 4 | 3, 4, 6 |
| | 6 | 21.7$^b$, CH$_3$ | 0.85$^b$, m | 4 | 3, 4, 5 |
| | NH | — | 8.23, d (7.7) | 2 | Leu$_2$-1 |
| Leu$_4$ | 1 | 172.0, qC | — | — | — |
| | 2 | 50.6, CH | 4.26, m | 3, NH | 1, 3, 4 |
| | 3 | 39.6, CH$_2$ | 1.51, m | 4 | 2, 4 |
| | 4 | 24.1$^b$, CH | 1.62$^b$, m | 3, 5, 6 | 3, 5, 6 |

TABLE 1-continued

NMR data (600 MHz, DMSO) of Xenobovide A
Colourless amorphous solid matter.
Optical activity: $[\alpha]^{25}_D$ −1.6° (c 0.25, MeOH)
HRESIMS: m/z 766.5075 [M + H]$^+$
(calculated for $C_{38}H_{68}N_7O_9$ 766.50785)

| Position | | $\delta_c$, mult. | $\delta_H$ (J in Hz) | COSY | HMBC |
|---|---|---|---|---|---|
| | 5 | 20.7$^b$, CH$_3$ | 0.81$^b$, m | 4 | 3, 4, 6 |
| | 6 | 20.7$^b$, CH$_3$ | 0.81$^b$, m | 4 | 3, 4, 5 |
| | NH | — | 7.51, d (8.9) | 2 | Leu$_3$-1 |
| BA$^a$ | 1 | 172.4, qC | — | — | — |
| | 2a | 44.5, CH$_2$ | 2.19, m | 2b, 3 | 1, 3, 4 |
| | 2b | 44.5, CH$_2$ | 2.11, m | 2a, 3 | 1, 3, 4 |
| | 3 | 25.6, CH | 2.00, m | 2a, 2b, 4 | 1, 2, 4 |
| | 4 | 13.9, CH$_3$ | 0.90, m | 3 | 3 |

$^a$BA: Butyric acid
$^b$the allocation can be exchanged

TABLE 2

NMR data (600 MHz, DMSO) of Xenobovid B
Colourless amorphous solid matter.
Optical activity: $[\alpha]^{25}_D$ −1.6° (c 0.25, MeOH)
HRESIMS: m/z 794.5380 [M + H]$^+$
(calculated for $C_{40}H_{72}N_7O_9$ 794.53915)

| Position | | $\delta_c$, mult. | $\delta_H$ (J in Hz) | COSY | HMBC |
|---|---|---|---|---|---|
| Thr | 1 | 169.2, qC | — | — | — |
| | 2 | 55.0, CH | 4.55, dd (2.1, 9.2) | 3, NH | 1, 3, 4, MPA-1 |
| | 3 | 70.6, CH | 5.21, qd (2.1, 6.3) | 2, 4 | 1, 4, Ala$_1$-1 |
| | 4 | 17.0, CH$_3$ | 1.15, d (6.3) | 3 | 2, 3 |
| | NH | — | 7.67, d (9.3) | 2 | 2, MPA-1 |
| Ala$_1$ | 1 | 171.7, qC | — | — | — |
| | 2 | 48.5, CH | 4.14, m | 3, NH | 1, 3 |
| | 3 | 16.0, CH$_3$ | 1.29, d (7.2) | 2 | 1, 2 |
| | NH | — | 8.13, d (5.5) | 2 | 2, Leu$_4$-1 |
| Ala$_2$ | 1 | 172.3, qC | — | — | — |
| | 2 | 49.2, CH | 4.19, m (6.7) | 3, NH | 1, 3, Thr-1 |
| | 3 | 17.9, CH$_3$ | 1.25, d (7.2) | 2 | 1, 2 |
| | NH | — | 7.96, d (6.2) | 2 | 2, Thr-1 |
| Leu$_1$ | 1 | 172.0, qC | — | — | — |
| | 2 | 52.0, CH | 4.11, m | 3, NH | 1, 3, 4 |
| | 3 | 39.0, CH$_2$ | 1.52, m | 4 | 2, 4 |
| | 4 | 24.2$^b$, CH | 1.62$^b$, m | 3, 5, 6 | 3, 5, 6 |
| | 5 | 23.0$^b$, CH$_3$ | 0.88$^b$, m | 4 | 3, 4, 6 |
| | 6 | 23.0$^b$, CH$_3$ | 0.88$^b$, m | 4 | 3, 4, 5 |
| | NH | — | 7.56, d (6.1) | 2 | Ala$_2$-1 |
| Leu$_2$ | 1 | 171.9, qC | — | — | — |
| | 2 | 52.3, CH | 4.08, m | 3, NH | 1, 3, 4 |
| | 3 | 39.5, CH$_2$ | 1.62, m | 4 | 2, 4 |
| | 4 | 24.2$^b$, CH | 1.62$^b$, m | 3, 5, 6 | 3, 5, 6 |
| | 5 | 22.5$^b$, CH$_3$ | 0.92$^b$, m | 4 | 3, 4, 6 |
| | 6 | 22.5$^b$, CH$_3$ | 0.92$^b$, m | 4 | 3, 4, 5 |
| | NH | — | 7.53, d (6.8) | 2 | Leu$_1$-1 |
| Leu$_3$ | 1 | 171.5, qC | — | — | — |
| | 2 | 51.5, CH | 4.13, m | 3, NH | 1, 3, 4 |
| | 3 | 39.5, CH$_2$ | 1.56, m | 4 | 2, 4 |
| | 4 | 24.1$^b$, CH | 1.62$^b$, m | 3, 5, 6 | 3, 5, 6 |
| | 5 | 21.7$^b$, CH$_3$ | 0.85$^b$, m | 4 | 3, 4, 6 |
| | 6 | 21.7$^b$, CH$_3$ | 0.85$^b$, m | 4 | 3, 4, 5 |
| | NH | — | 8.24, d (7.9) | 2 | Leu$_2$-1 |
| Leu$_4$ | 1 | 171.9, qC | — | — | — |
| | 2 | 50.5, CH | 4.25, m | 3, NH | 1, 3, 4 |
| | 3 | 39.6, CH$_2$ | 1.50, m | 4 | 2, 4 |
| | 4 | 24.0$^b$, CH | 1.62$^b$, m | 3, 5, 6 | 3, 5, 6 |
| | 5 | 20.7$^b$, CH$_3$ | 0.81$^b$, m | 4 | 3, 4, 6 |
| | 6 | 20.7$^b$, CH$_3$ | 0.81$^b$, m | 4 | 3, 4, 5 |
| | NH | — | 7.50, d (8.7) | 2 | Leu$_3$-1 |
| MPA$^a$ | 1 | 172.6, qC | — | — | — |
| | 2a | 35.0, CH$_2$ | 2.28, m | 2b, 3 | 1, 3, 4 |
| | 2b | 35.0, CH$_2$ | 2.19, m | 2a, 3 | 1, 3, 4 |
| | 3 | 24.8, CH | 1.51, m | 2a, 2b, 4, 6 | 1, 2, 4, 6 |

TABLE 2-continued

NMR data (600 MHz, DMSO) of Xenobovid B
Colourless amorphous solid matter.
Optical activity $[\alpha]^{25}_D$ −1.6° (c 0.25, MeOH)
HRESIMS: m/z 794.5380 [M + H]$^+$
(calculated for $C_{40}H_{72}N_7O_9$ 794.53915)

| Position | $\delta_c$, mult. | $\delta_H$ (J in Hz) | COSY | HMBC |
|---|---|---|---|---|
| 4 | 30.7, CH$_2$ | 1.24, m | 3, 5 | 3, 5 |
| 5 | 13.1, CH$_3$ | 0.85, m | 4 | 4 |
| 6 | 21.4, CH$_3$ | 1.28, m | 3 | 3 |

$^a$MPA: 3-Methyl valeric acid
$^b$the allocation can be exchanged

TABLE 3

NMR data (600 MHz, DMSO) of Xenobovide C
Colourless amorphous solid matter.
Optical activity $[\alpha]^{25}_D$ −2.4° (c 0.25, MeOH)
HRESIMS: m/z 808.5545 [M + H]$^+$
(calculated for $C_{41}H_{74}N_7O_9$ 808.55480)

| Position | | $\delta_c$, mult. | $\delta_H$ (J in Hz) | COSY | HMBC |
|---|---|---|---|---|---|
| Thr | 1 | 169.0, qC | — | — | — |
| | 2 | 55.1, CH | 4.55, dd (2.0, 9.3) | 3, NH | 1, 3, 4, MHA-1 |
| | 3 | 70.6, CH | 5.22, qd (2.0, 6.3) | 2, 4 | 1, 4, Ala$_1$-1 |
| | 4 | 17.1, CH$_3$ | 1.16, d (6.3) | 3 | 2, 3 |
| | NH | — | 7.69, d (9.3) | 2 | 2, MHA-1 |
| Ala$_1$ | 1 | 171.8, qC | — | — | — |
| | 2 | 48.5, CH | 4.15, m | 3, NH | 1, 3 |
| | 3 | 16.0, CH$_3$ | 1.29, d(7.1) | 2 | 1, 2 |
| | NH | — | 8.14, d (5.4) | 2 | 2, Leu$_4$-1 |
| Ala$_2$ | 1 | 172.4, qC | — | — | — |
| | 2 | 49.4, CH | 4.19, m (6.7) | 3, NH | 1, 3, Thr-1 |
| | 3 | 18.0, CH$_3$ | 1.25, d (7.2) | 2 | 1, 2 |
| | NH | — | 7.97, d (6.2) | 2 | 2, Thr-1 |
| Leu$_1$ | 1 | 172.1, qC | — | — | — |
| | 2 | 52.1, CH | 4.13, m | 3, NH | 1, 3, 4 |
| | 3 | 39.0, CH$_2$ | 1.53, m | 4 | 2, 4 |
| | 4 | 24.2$^b$, CH | 1.63$^b$, m | 3, 5, 6 | 3, 5, 6 |
| | 5 | 23.0$^b$, CH$_3$ | 0.88$^b$, m | 4 | 3, 4, 6 |
| | 6 | 23.0$^b$, CH$_3$ | 0.88$^b$, m | 4 | 3, 4, 5 |
| | NH | — | 7.58, d (6.0) | 2 | Ala$_2$-1 |
| Leu$_2$ | 1 | 172.0, qC | — | — | — |
| | 2 | 52.4, CH | 4.09, m | 3, NH | 1, 3, 4 |
| | 3 | 39.5, CH$_2$ | 1.63, m | 4 | 2, 4 |
| | 4 | 24.2$^b$, CH | 1.63$^b$, m | 3, 5, 6 | 3, 5, 6 |
| | 5 | 22.5$^b$, CH$_3$ | 0.92$^b$, m | 4 | 3, 4, 6 |
| | 6 | 22.5$^b$, CH$_3$ | 0.92$^b$, m | 4 | 3, 4, 5 |
| | NH | — | 7.54, d (6.7) | 2 | Leu$_1$-1 |
| Leu$_3$ | 1 | 171.6, qC | — | — | — |
| | 2 | 51.6, CH | 4.14, m | 3, NH | 1, 3, 4 |
| | 3 | 39.5, CH$_2$ | 1.59, m | 4 | 2, 4 |
| | 4 | 24.1$^b$, CH | 1.63$^b$, m | 3, 5, 6 | 3, 5, 6 |
| | 5 | 21.7$^b$, CH$_3$ | 0.85$^b$, m | 4 | 3, 4, 6 |
| | 6 | 21.7$^b$, CH$_3$ | 0.85$^b$, m | 4 | 3, 4, 5 |
| | NH | — | 8.24, d (7.7) | 2 | Leu$_2$-1 |
| Leu$_4$ | 1 | 172.0, qC | — | — | — |
| | 2 | 50.6, CH | 4.26, m | 3, NH | 1, 3, 4 |
| | 3 | 39.6, CH$_2$ | 1.51, m | 4 | 2, 4 |
| | 4 | 24.0$^b$, CH | 1.63$^b$, m | 3, 5, 6 | 3, 5, 6 |
| | 5 | 20.7$^b$, CH$_3$ | 0.82$^b$, m | 4 | 3, 4, 6 |
| | 6 | 20.7$^b$, CH$_3$ | 0.82$^b$, m | 4 | 3, 4, 5 |
| | NH | — | 7.51, d (8.8) | 2 | Leu$_3$-1 |
| MHA$^a$ | 1 | 172.7, qC | — | — | — |
| | 2a | 35.3, CH$_2$ | 2.29, m | 2b, 3 | 1, 3, 4 |
| | 2b | 35.3, CH$_2$ | 2.20, m | 2a, 3 | 1, 3, 4 |
| | 3 | 23.1, CH | 1.51, m | 2a, 2b, 4, 7 | 1, 2, 4, 7 |
| | 4 | 37.9, CH$_2$ | 1.15, m | 3, 5 | 3, 5 |
| | 5 | 27.1, CH$_2$ | 1.51, m | 4, 6 | 4, 6 |

TABLE 3-continued

NMR data (600 MHz, DMSO) of Xenobovide C
Colourless amorphous solid matter.
Optical activity $[\alpha]^{25}_D$ −2.4° (c 0.25, MeOH)
HRESIMS: m/z 808.5545 [M + H]$^+$
(calculated for $C_{41}H_{74}N_7O_9$ 808.55480)

| Position | $\delta_c$, mult. | $\delta_H$ (J in Hz) | COSY | HMBC |
|---|---|---|---|---|
| 6 | 23.1, $CH_3$ | 0.85, m | 5 | 5, 7 |
| 7 | 22.4, $CH_3$ | 0.88, m | 3 | 3 |

$^a$MHA: 3-Methyl hexanoic acid
$^b$the allocation can be exchanged

The invention claimed is:

1. A compound having the general structure

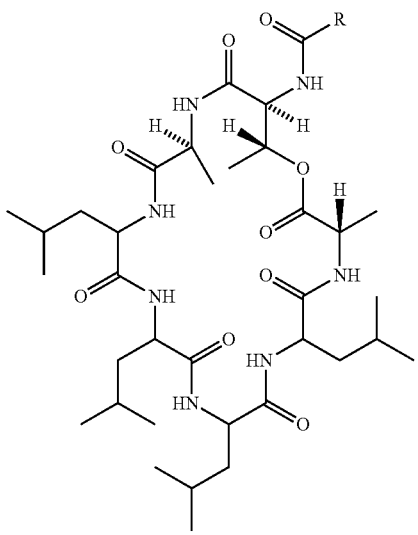

wherein

R is selected from the group consisting of a hydrogen atom (H), an unsubstituted, monosubstituted or polysubstituted $C_1$-$C_{20}$-alkyl, wherein the alkyl is straight, branched, cyclic and/or partially unsaturated; and an unsubstituted, monosubstituted or multisubstituted phenyl residue.

2. The compound according to claim 1, wherein the substituents of R are selected from the group consisting of a linear or branched alkyl group, an acyl group, a halogen, an unsubstituted or alkyl-substituted amino group, a hydroxyl group, an ether group, a free carboxyl group, a carboxyl group esterified with an alkyl group, and an amidated carboxyl group.

3. The compound according to claim 2, wherein the acyl group is selected from the group consisting of formyl, acetyl, trichloroacetyl, fumaryl, maleyl, succinyl, benzoyl, a branched acyl group, and an acyl group substituted with a heteroatom or an aryl group.

4. The compound according to claim 1, having a formula selected from the group consisting of Xenobovide A

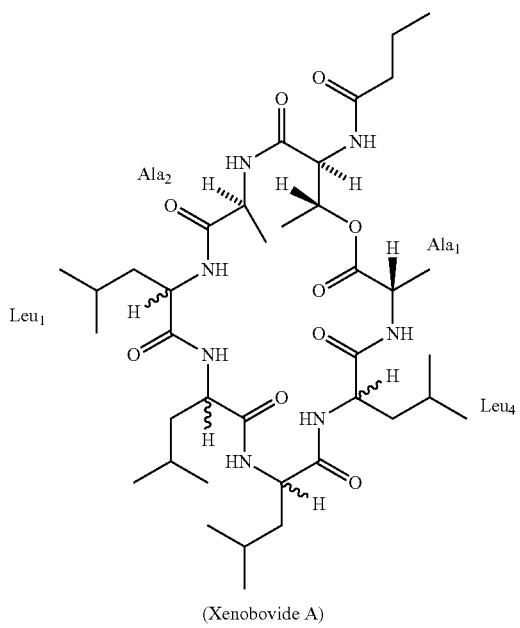

(Xenobovide A)

and diastereomers thereof.

5. The compound according to claim 1, having a formula selected from the group consisting of Xenobovide B

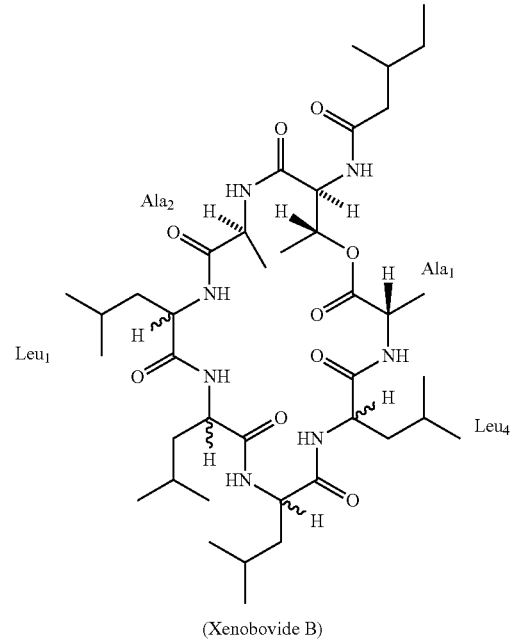

(Xenobovide B)

and diastereomers thereof.

6. A pharmaceutical composition comprising a compound of claim 1.

7. The compound according to claim 1, having a formula selected from the group consisting of Xenobovide C

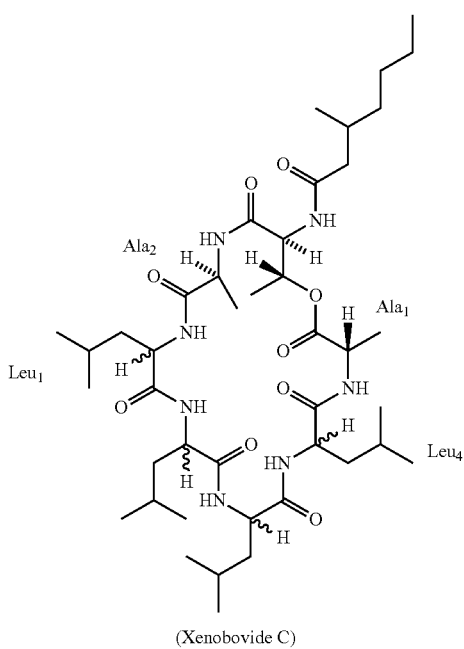

(Xenobovide C)

and diastereomers thereof.

8. A method for production of a compound according to claim 1, comprising the steps of
cultivating a bacterium of the genus *Xenorhabdus*; and
isolating the compound from the culture medium and/or the bacterium.

9. The method according to claim 8, wherein the bacterium is *Xenorhabdus bovienii*.

10. A method for the treatment of cancer, the method comprising administering to a subject in need thereof a therapeutically effective amount of a compound according to claim 1, wherein the cancer is selected from the group consisting of melanoma, gastric cancer, lung cancer, breast cancer, pancreatic cancer, kidney cancer and intestinal cancer.

11. A method of inhibiting an enzyme selected from the group consisting of acetylcholinesterase, phosphodiesterase, protein tyrosine phosphatase and glycogen synthase kinase 3beta, the method comprising contacting said enzyme with a compound according to claim 1.

12. A method for repelling the proliferation of a pest organism, wherein the pest organism is a wax moth, the method comprising contacting the pest organism with a compound according to claim 1.

13. A method for inhibiting the growth of a phytopathogenic bacterium, the method comprising contacting the phytopathogenic bacterium with a compound according to claim 1, wherein the phytopathogenic bacterium is *Xanthomonas campestris*.

14. A method for the treatment of a subject having a neurological disease selected from the group consisting of Alzheimer's disease, Myasthenia Gravis, bipolar disorder, and schizophrenia, comprising administering to said subject a therapeutically effective amount of a compound according to claim 1, wherein said compound inhibits acetylcholine esterase, phosphodiesterase PDE-4B2 and/or glycogen synthase kinase 3beta.

15. A method for the treatment of a subject having diabetes and/or obesity, comprising administering to said subject a therapeutically effective amount of a compound according to claim 1, wherein said compound inhibits protein tyrosine phosphatase 1B and/or glycogen synthase kinase 3beta.

16. A method for the treatment of a subject having an inflammatory lung disease selected from the group consisting of asthma, chronic obstructive bronchitis, lung emphysema and rhinitis, comprising administering to said subject a therapeutically effective amount of a compound according to claim 1, wherein said compound inhibits phosphodiesterase PDE-4B2.

17. A method for the treatment of a subject infected with HIV, comprising administering to said subject a therapeutically effective amount of a compound according to claim 1, wherein said compound inhibits phosphodiesterase PDE-4B2.

18. A method for the treatment of a subject having alopecia, comprising administering to said subject a therapeutically effective amount of a compound according to claim 1, wherein said compound inhibits glycogen synthase kinase 3beta.

19. A method for the treatment of a subject infected with a gram positive bacterium, comprising administering to said subject a therapeutically effective amount of a compound according to claim 1, wherein the gram positive bacterium is *Staphylococcus xylosus* or *Bacillus subtilis*.

* * * * *